(12) United States Patent
Chon et al.

(10) Patent No.: US 9,052,295 B2
(45) Date of Patent: Jun. 9, 2015

(54) PANEL INSPECTION METHOD AND APPARATUS

(71) Applicant: Samsung Techwin Co., Ltd., Changwon (KR)

(72) Inventors: Je-Youl Chon, Changwon (KR); Jun-Ho Cha, Changwon (KR); Jae-Ho Jeong, Changwon (KR); Yun-Won Park, Changwon (KR)

(73) Assignee: SAMSUNG TECHWIN CO., LTD., Changwon-Si (KR)

( * ) Notice: Subject to any disclaimer, the term of this patent is extended or adjusted under 35 U.S.C. 154(b) by 118 days.

(21) Appl. No.: 13/973,352

(22) Filed: Aug. 22, 2013

(65) Prior Publication Data

US 2014/0307944 A1 Oct. 16, 2014

(30) Foreign Application Priority Data

Apr. 11, 2013 (KR) .................... 10-2013-0040023

(51) Int. Cl.
  *G06T 7/00* (2006.01)
  *G01N 21/88* (2006.01)
  *G01N 21/95* (2006.01)
(52) U.S. Cl.
  CPC ............ *G01N 21/8851* (2013.01); *G01N 21/95* (2013.01)

(58) Field of Classification Search
  None
  See application file for complete search history.

(56) References Cited

U.S. PATENT DOCUMENTS

| | | | |
|---|---|---|---|
| 2005/0167620 A1* | 8/2005 | Cho et al. | 250/559.45 |
| 2006/0222232 A1* | 10/2006 | Ishikawa | 382/141 |
| 2007/0047801 A1* | 3/2007 | Kojima et al. | 382/149 |
| 2008/0063254 A1* | 3/2008 | Tanizaki et al. | 382/141 |

FOREIGN PATENT DOCUMENTS

| | | |
|---|---|---|
| JP | 08-271436 A | 10/1996 |
| KR | 10-0381134 B1 | 4/2003 |
| KR | 10-2009-0006456 A | 1/2009 |

* cited by examiner

*Primary Examiner* — Bhavesh Mehta
*Assistant Examiner* — David F Dunphy
(74) *Attorney, Agent, or Firm* — Sughrue Mion, PLLC

(57) ABSTRACT

Provided are a panel inspection method and apparatus, the panel inspection method including: (a) determining if a variance value of luminance of a captured image of a panel is greater than a reference value, and searching for an original image and at least one secondary reflective image of a defect of the panel if it is determined that the variance value is greater than the reference value; and (b) determining whether the defect is an actual defect or an impurity disposed on the panel based on at least one of a difference in a luminance characteristic between the original image and the secondary reflective image and a number of the searched secondary reflective image.

20 Claims, 11 Drawing Sheets

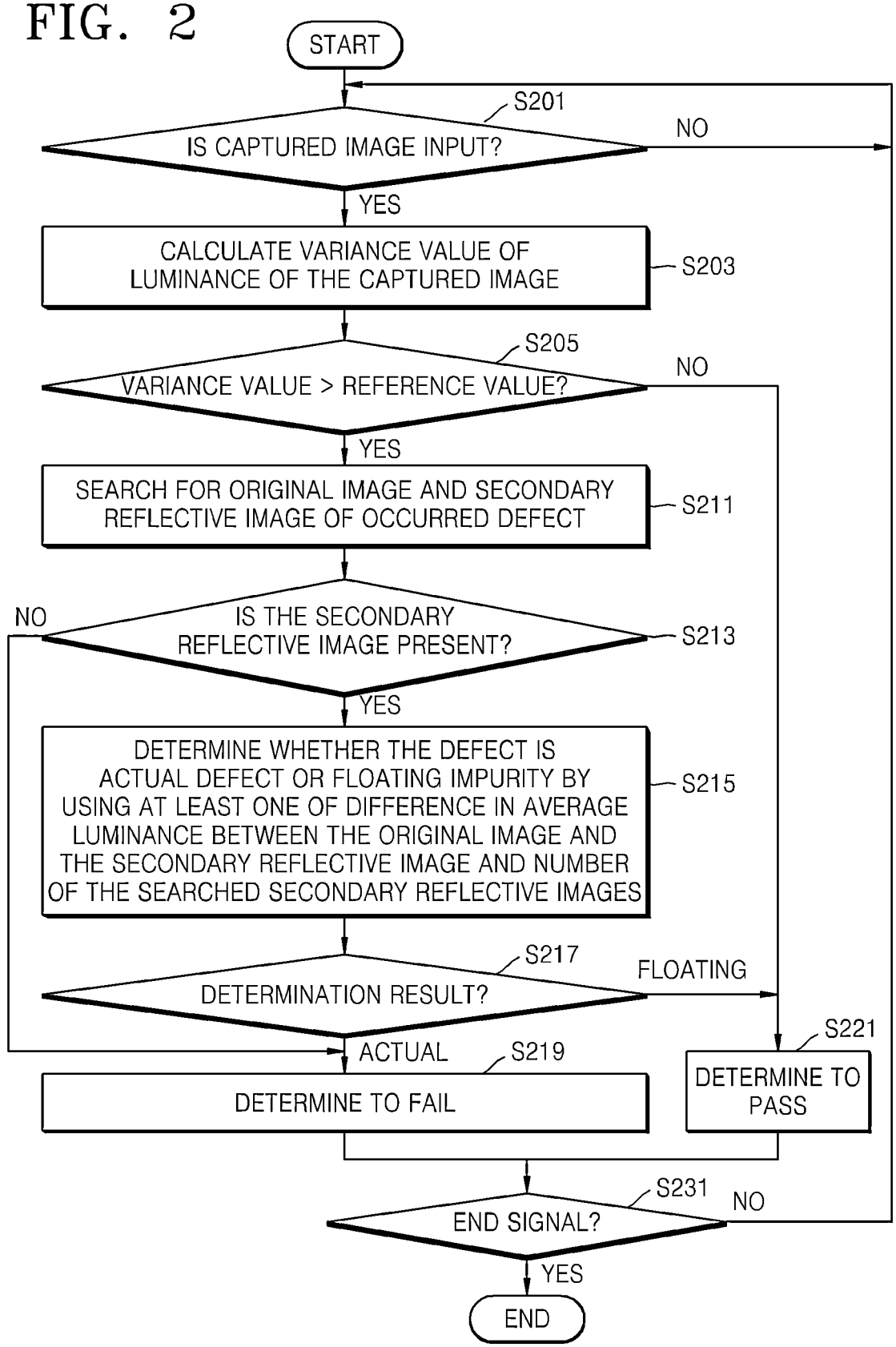

FIG. 3

| | IMAGE CHARACTERISTIC OF FLOATING IMPURITY | | IMAGE CHARACTERISTIC OF ACTUAL DEFECT | |
|---|---|---|---|---|
| | ORIGINAL IMAGE | SECONDARY REFLECTIVE IMAGE | ORIGINAL IMAGE | SECONDARY REFLECTIVE IMAGE |
| VERTICAL LOCATION — 301 | HIGH | LOW | HIGH | LOW |
| NUMBER — 302 | 1 | SAME OR MORE THAN 1 | 1 | SAME OR LESS THAN 1 |
| AVERAGE LUMINANCE (TRANSPARENT IMPURITY, DEFECT) — 303a | LOW | HIGH | MIDDLE | MIDDLE |
| AVERAGE LUMINANCE (NON-TRANSPARENT IMPURITY) — 303b | HIGH | LOW | N/A | N/A |

FIG. 4

| CAPTURED IMAGE | BINARY IMAGE | NUMBER | INTERVAL | LUMINANCE DIFFERENCE |
|---|---|---|---|---|
| 401 | 402, 402a, 402b | ORIGINAL IMAGE : 1<br>SECONDARY REFLECTIVE IMAGE : 1 | 45 | 37 |
| 411 | 412, 412a, 412b, 412c, 412d | ORIGINAL IMAGE : 1<br>SECONDARY REFLECTIVE IMAGE : 3 | 48 | 42 |
| 421 | 422, 422a, 422b | ORIGINAL IMAGE : 1<br>SECONDARY REFLECTIVE IMAGE : 1 | 55 | 19 |
| 431 | 432, 432a, 432b | ORIGINAL IMAGE : 1<br>SECONDARY REFLECTIVE IMAGE : 1 | 52 | 24 |

FIG. 5

| CAPTURED IMAGE | BINARY IMAGE | NUMBER | INTERVAL | LUMINANCE DIFFERENCE |
|---|---|---|---|---|
| 501 | 502, 502a, 502c, 502b, 502d | ORIGINAL IMAGE : 1<br>SECONDARY REFLECTIVE IMAGE : 3 | 32 | 37 |
| 511 | 512, 512a, 512b | ORIGINAL IMAGE : 1<br>SECONDARY REFLECTIVE IMAGE : 1 | 47 | 42 |
| 521 | 522, 522a, 522b | ORIGINAL IMAGE : 1<br>SECONDARY REFLECTIVE IMAGE : 1 | 48 | 19 |
| 531 | 532, 532a, 532b | ORIGINAL IMAGE : 1<br>SECONDARY REFLECTIVE IMAGE : 1 | 47 | 24 |

FIG. 6

| CAPTURED IMAGE | BINARY IMAGE | NUMBER | INTERVAL | LUMINANCE DIFFERENCE |
|---|---|---|---|---|
| 601 | 602a, 602b, 602 | ORIGINAL IMAGE : 1<br>SECONDARY REFLECTIVE IMAGE : 1 | 45 | 8 |
| 611 | 612a, 612b, 612 | ORIGINAL IMAGE : 1<br>SECONDARY REFLECTIVE IMAGE : 1 | 49 | 6 |
| 621 | 622a, 622b, 622 | ORIGINAL IMAGE : 1<br>SECONDARY REFLECTIVE IMAGE : 1 | 48 | 0 |
| 631 | 632a, 632b, 632 | ORIGINAL IMAGE : 1<br>SECONDARY REFLECTIVE IMAGE : 1 | 51 | 7 |

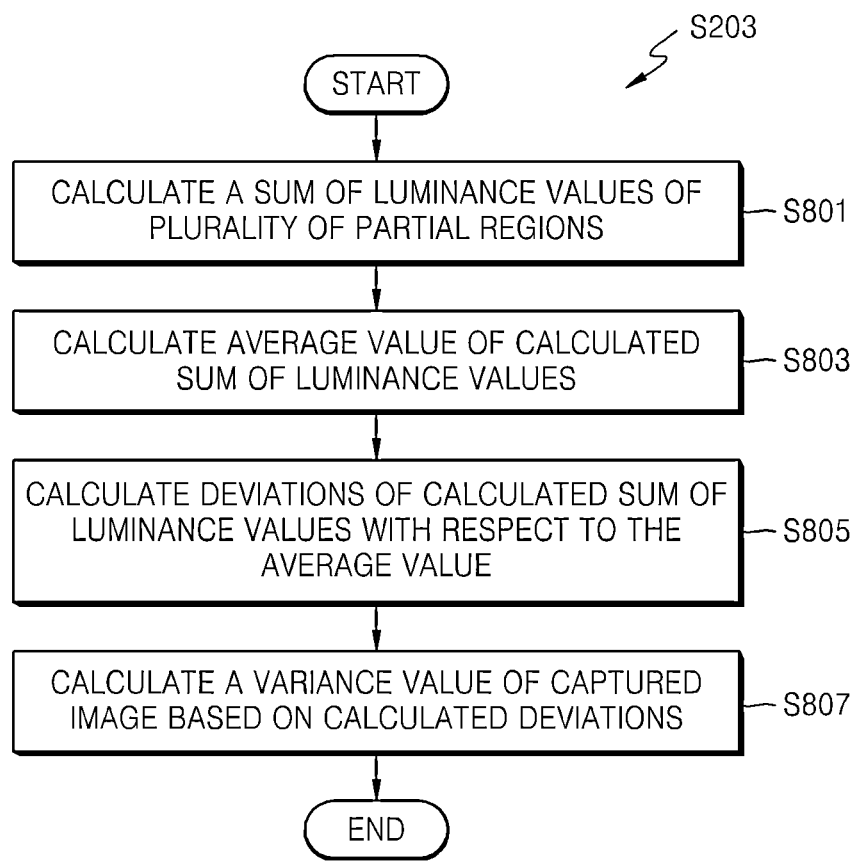

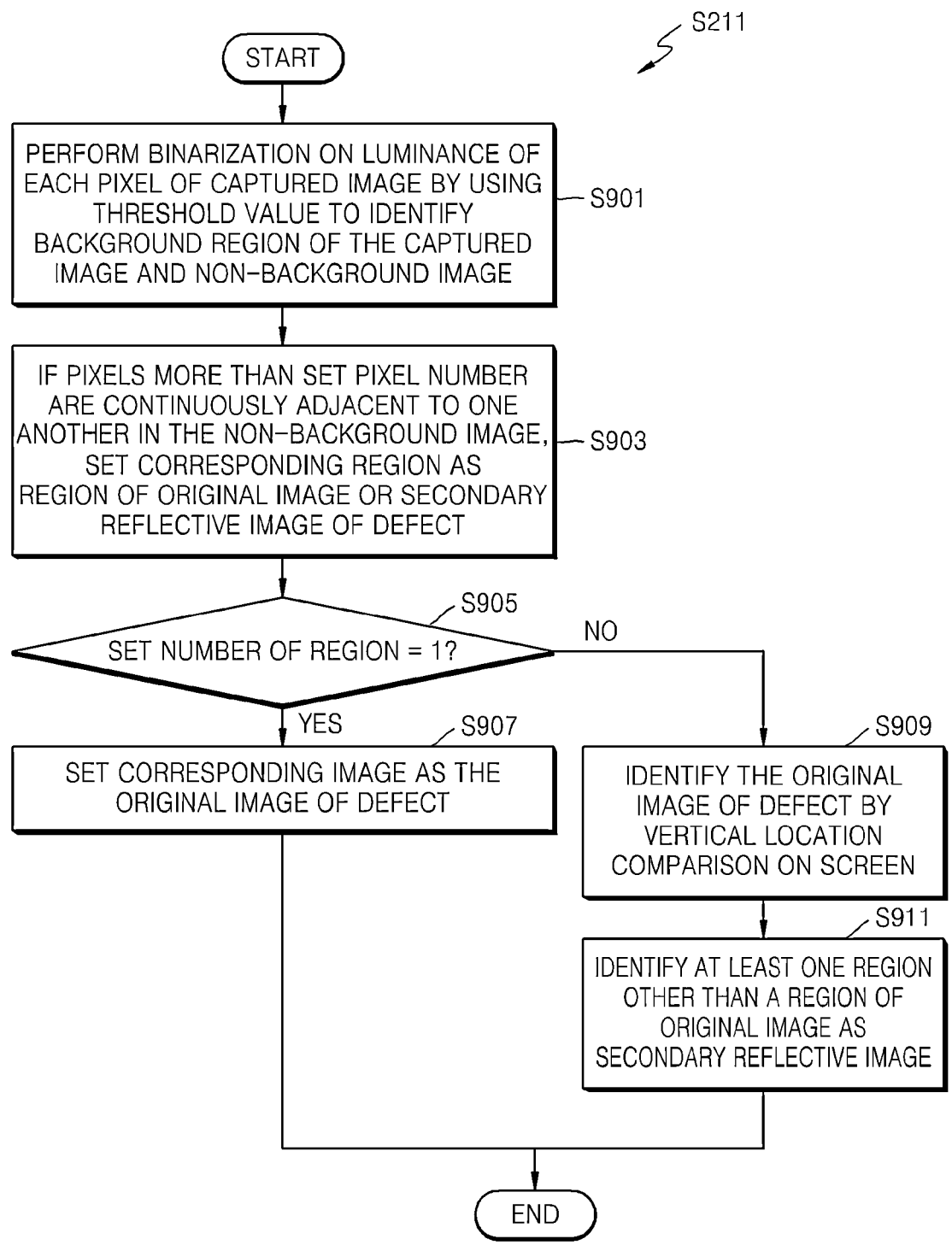

FIG. 10

| | | | | | | | | | | |
|---|---|---|---|---|---|---|---|---|---|---|
| 0 | 0 | 0 | 0 | 0 | 0 | 0 | 0 | 0 | 0 | 0 |
| 0 | 0 | 0 | 0 | 0 | 0 | 0 | 0 | 0 | 0 | 0 |
| 0 | 0 | 0 | 0 | 0 | 0 | 0 | 0 | 0 | 0 | 0 |
| 0 | 0 | 0 | 0 | 1 | 1 | 1 | 1 | 0 | 0 | 0 |
| 0 | 0 | 0 | 1 | 1 | 1 | 1 | 1 | 1 | 0 | 0 |
| 0 | 0 | 0 | 1 | 1 | 0 | 0 | 1 | 1 | 0 | 0 |
| 0 | 0 | 0 | 0 | 0 | 0 | 0 | 0 | 0 | 0 | 0 |
| 0 | 0 | 0 | 0 | 0 | 0 | 0 | 0 | 0 | 0 | 0 |
| 0 | 0 | 0 | 0 | 1 | 1 | 1 | 0 | 0 | 0 | 0 |
| 0 | 0 | 0 | 0 | 0 | 1 | 1 | 1 | 0 | 0 | 0 |
| 0 | 0 | 0 | 0 | 0 | 0 | 0 | 0 | 0 | 0 | 0 |

PANEL INSPECTION METHOD AND APPARATUS

CROSS-REFERENCE TO RELATED PATENT APPLICATION

This application claims priority from Korean Patent Application No. 10-2013-0040023, filed on Apr. 11, 2013, in the Korean Intellectual Property Office, the disclosure of which is incorporated herein in its entirety by reference.

BACKGROUND

1. Field

Methods and apparatuses consistent with exemplary embodiments relate to panel inspection, and more particularly, to analyzing a captured image of a panel in which a lower plate and an upper plate formed of different materials are coupled to each other and determining whether the panel has an actual defect.

2. Description of the Related Art

A representative example of a panel in which a lower plate and an upper plate formed of different materials are coupled to each other may be a light emitting diode (LED) display panel.

During a process of manufacturing the panel, a physical defect such as a scratch may occur on the panel. To inspect such defect, after a captured image of the panel is obtained, it is determined whether the panel is defective according to a variance value of luminance of the capture image. That is, if the variance value of luminance of the captured image is greater than a reference value, the panel is determined to fail in the inspection.

However, although an inspection target panel has no actual defect, there are many cases in which the inspection target panel is determined to fail in an inspection. Such problem is a major cause of deterioration of productivity of a panel.

It may be considered to increase the reference value with respect to a variance value of luminance to solve the above problem. In this case, however, although the inspection target panel has an actual defect, the inspection target panel may be determined to pass the inspection.

Therefore, simply increasing the reference value with respect to the variance value of luminance is not a fundamental solution to address the above problem.

SUMMARY

One or more exemplary embodiments of the present inventive concept provide a panel inspection method of minimizing a failure frequency of an inspection target panel even if the inspection target panel has no actual defect, and a panel inspection apparatus employing the panel inspection method.

According to an aspect of an exemplary embodiment, there is provided a panel inspection method. The method may apply to inspecting a panel in which a lower plate and an upper plate that are formed of different materials are coupled to each other.

The panel inspection method includes: (a) determining if a variance value of luminance of a captured image of a panel is greater than a reference value, and searching for an original image and at least one secondary reflective image of a defect of the panel if it is determined that the variance value is greater than the reference value; and (b) determining whether the defect is an actual defect or an impurity disposed on the panel based on at least one of a difference in a luminance characteristic between the original image and the secondary reflective image and a number of the searched secondary reflective image.

The method may further include calculating the variance value of luminance of the captured image in operation, wherein the calculating the variance value may include: partitioning a region of the captured image into a plurality of partial regions; calculating a sum of luminance values of the plurality of partial regions; calculating an average value of the calculated sum of the luminance values; calculating deviations of the sum of the luminance values with respect to the average value of the calculated sum of the luminance values; and obtaining the variance value of the luminance of the captured image of the panel.

Operation (b) may include determining the defect as the actual defect if it is determined that there is no secondary reflective image as a result of the searching for the original image and the secondary reflective image of the defect.

The searching for the original image and the secondary reflective image of the defect in operation (a) may include: performing binarization on a luminance of each pixel of the captured image by using a threshold value to identify a background region and a non-background region of the captured image; determining if pixels more than a set number are continuously adjacent to one another in the non-background region; and setting the non-background region as a region of the original image or the secondary reflective image of the defect if it is determined that pixels more than the set number are continuously adjacent to one another in the non-background region.

Operation (a) may further include: determining if more than one region is set as the region of the original image or the secondary reflective image of the defect; and if it is determined that more than one region is set, identifying regions of the original image and the secondary reflective image by a vertical location comparison on a screen of the captured image.

Operation (b) may further include determining the defect as the impurity, if it is determined that there is more than one secondary reflective image as a result of the searching for the original image and the secondary reflective image of the defect.

Operation (b) may further include determining the defect as the impurity if it is determined that a difference in average luminance between the original image and the secondary reflective image is greater than a predetermined value.

Operation (b) may include: determining if the number of the searched secondary reflective image is more than one; determining if a difference in average luminance between the original image and the more than one secondary reflective image is greater than a predetermined value; and determining the occurred defect as the impurity if it is determined that the difference in average luminance between the original image and the more than one secondary reflective image is greater than the predetermined value.

Operation (b) may include: determining if the number of the searched secondary reflective image more than one; determining if a difference in average luminance between the original image and a representative secondary reflective image among the more than one secondary reflective image is greater than a predetermined value; and determining the defect as the impurity if it is determined that the difference in average luminance between the original image and the representative secondary reflective image is greater than the predetermined value.

In operation (b), the secondary reflective representative image may be the largest image among the more than one secondary reflective image.

According to an aspect of another exemplary embodiment, there is provided a panel inspection apparatus. The panel inspection apparatus may be used to inspect a panel in which a lower plate and an upper plate that are formed of different materials are coupled to each other The panel inspection apparatus may include: a defect determining unit configured to analyze a captured image of a panel and determine whether a defect is present in the panel, wherein the defect determining unit is further configured to determine if a variance value of luminance of the captured image is greater than a reference value, and search for an original image and at least one secondary reflective image of the defect of the panel if it is determined that the variance value is greater than the reference value; and determine whether the defect is an actual defect or a impurity based on at least one of a difference in a luminance characteristic between the original image and the secondary reflective image and a number of the searched secondary reflective image.

BRIEF DESCRIPTION OF THE DRAWINGS

The above and other aspects will become more apparent by describing in detail exemplary embodiments with reference to the attached drawings, in which:

FIG. 2 is a flowchart of a panel inspection method employed in a defect determining unit of FIG. 1 according to an exemplary embodiment;

FIG. 3 is a table of experiment results that are a basis for the panel inspection method of FIG. 2, according to an exemplary embodiment;

FIG. 4 is a table of experiment results regarding first through fourth floating impurities relating to the experiment results of FIG. 3, according to an exemplary embodiment;

FIG. 5 is a table of experiment results regarding fifth through eighth floating impurities relating to the experiment results of FIG. 3, according to an exemplary embodiment;

FIG. 6 is a table of experiment results regarding first through fourth actual defects relating to the experiment results of FIG. 3, according to an exemplary embodiment;

FIG. 7 shows a plurality of partial regions partitioned from an overall region of a captured image to perform operation S203 of FIG. 2, according to an exemplary embodiment;

FIG. 8 is a detailed flowchart of operation S203 of FIG. 2, according to an exemplary embodiment;

FIG. 9 is a detailed flowchart of operation S211 of FIG. 2, according to an exemplary embodiment;

FIG. 10 shows a binary image obtained by performing operation S901 of FIG. 9, according to an exemplary embodiment;

DETAILED DESCRIPTION

The inventive concept will now be described more fully with reference to the accompanying drawings, in which exemplary embodiments of the invention are shown. The inventive concept may, however, be embodied in many different forms and should not be construed as being limited to the embodiments set forth herein.

Figure 1:
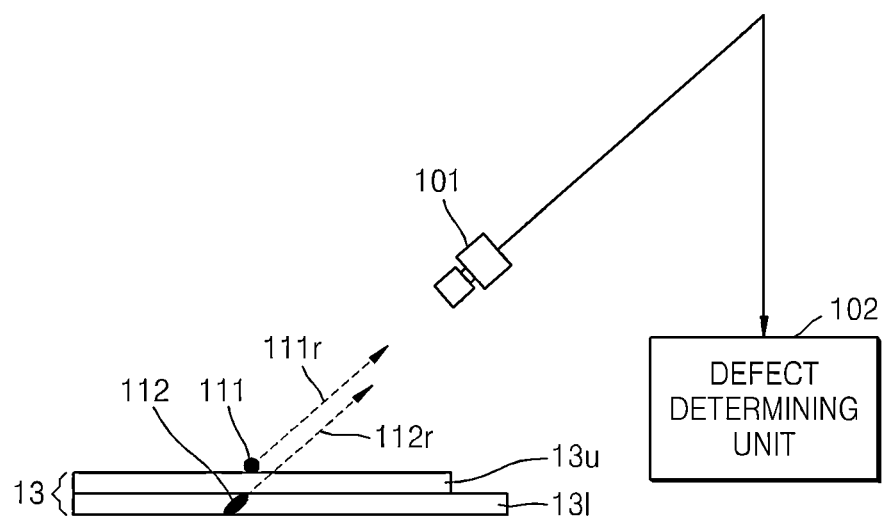
FIG. 1 shows a panel inspection apparatus according to an exemplary embodiment.

FIG. 1 shows a panel inspection apparatus according to an exemplary embodiment.

Referring to FIG. 1, an inspection target panel of the panel inspection apparatus according to an exemplary embodiment is a panel 13 in which a lower plate 13l and an upper plate 13u that are formed of different materials, for example, a light emitting diode (LED) display panel.

The panel inspection apparatus of the present embodiment analyzes a captured image of the inspection target panel 13, and determines whether the inspection target panel 13 has an actual defect. For these operations, the panel inspection apparatus of the present embodiment includes a photographing unit 101 and a defect determining unit 102.

The photographing unit 101 photographs the inspection target panel 13 from above the upper plate 13u of the inspection target panel 13 and obtains the captured image. The defect determining unit 102 analyzes the captured image from the photographing unit 101 and determines whether the inspection target panel 13 has an actual defect.

If a defect 111 is present at the upper plate 13u of the inspection target panel 13, the photographing unit 101 may obtain an original image of the defect 111 by a primary reflective light 111r from the defect 111. In addition, due to the lower plate 13l and the upper plate 13u that are formed of different materials, the photographing unit 101 may obtain a secondary reflective image of the defect 111 by a secondary reflective light 112r from a secondary reflective region 112.

According to an experiment for the present embodiment, if the defect 111 is a floating impurity, the secondary reflective image may be one like the original image or may be plural due to scattering of the secondary reflective light 112r.

Meanwhile, if the defect 111 is an actual defect on the upper plate 13u like a physical or chemical defect such as a scratch, the secondary reflective image may be one like the original image or may be none.

If the defect 111 is the floating impurity, a difference in average luminance between the original image and the secondary reflective image may be dramatically great.

Meanwhile, if the defect 111 is an actual defect on the upper plate 13u like a physical or chemical defect such as scratch, the difference in average luminance between the original image and the secondary reflective image may be dramatically small.

Accordingly, if a variance value of luminance of the captured image is greater than a reference value, the defect determining unit 102 of the present embodiment searches for the original image and the secondary reflective image of the defect 111, and determines whether the defect 111 is an actual defect or a floating impurity by using at least one of the difference in average luminance between the original image and the secondary reflective image and the number of the searched secondary reflective images. In this regard, a panel inspection method will be described in detail with reference to FIGS. 2 through 12.

Therefore, the panel inspection method of the present embodiment and the panel inspection apparatus employing the panel inspection method may determine whether the defect 111 is an actual defect by using a difference in characteristics, such as an average luminance, between the original image and the secondary reflective image of the defect 111 although a variance value of luminance of the captured image is greater than the reference value. That is, if the defect 111 is the floating impurity, an inspection target panel may be determined to pass the inspection.

Thus, even if the inspection target panel has no actual defect, a failure frequency of the inspection target panel may be minimized, thereby increasing panel productivity.

FIG. 2 is a flowchart of a panel inspection method employed in the defect determining unit 102 of FIG. 1 according to an exemplary embodiment. The panel inspection method employed in the defect determining unit 102 will now be described with reference to FIGS. 1 and 2.

If a captured image of the panel inspection panel 13 is input into the defect determining unit 102 from the photographing unit 101 (S201), the defect determining unit 102 calculates a variance value of luminance of the captured image (S203). This operation S203 will be described in more detail with reference to FIGS. 7 and 8.

If the variance value of luminance of the captured image is not greater than a reference value (S205), the defect determining unit 102 determines the inspection target panel 13 as having no defect, that is, passing the inspection (operation S221).

If the variance value of brightness of the captured image is greater than the reference value, since the inspection target panel 13 has the defect 111, the defect determining unit 102 performs a detailed investigation process from operations S211 through S221.

In operation S211, the defect determining unit 102 searches for an original image and a secondary reflective image of the defect 111. This operation S211 will be described in detail with reference to FIGS. 9 and 10.

In this regard, if there is no secondary reflective image, the defect determining unit 102 determines that the inspection target panel 13 as having a defect, that is, failing in the inspection (S213 and S221). If there is no secondary reflective image, the defect 111 is regarded as an actual defect on the upper plate 13u like a physical or a chemical defect such as scratch. That is, if the defect 111 is a floating impurity, there is at least one secondary reflective image.

If there is a secondary reflective image in operation S213, the defect determining unit 102 performs operations S215 through S221 for the detailed investigation process.

In operation S215, the defect determining unit 102 determines whether the defect 111 is an actual defect or a floating impurity by using at least one of a difference in average luminance between the original image and the secondary reflective image and the number of searched secondary reflective images. This operation S215 will be described in detail with reference to FIGS. 11 and 12.

As a result of determination in operation S215, if the defect 111 is a floating impurity, the defect determining unit 102 determines that the inspection target panel 13 as having no defect, that is, passing the inspection (S217 and S219).

As a result of determination in operation S215, if the defect 111 is an actual defect, the defect determining unit 102 determines that the inspection target panel 13 as having a defect, that is, failing in the inspection (S217 and S221).

The above-described operations S201 through S221 are repeatedly performed until an end signal is generated (S231).

FIG. 3 is a table of experiment results that are a basis for the panel inspection method of FIG. 2.

FIG. 4 is a table of experiment results regarding first through fourth floating impurities relating to the experiment results of FIG. 3. Referring to FIG. 4, reference numerals 401, 411, 421, and 431 denote captured images of a panel having a floating impurity. Reference numerals 402, 412, 422, and 432 denote binary images. A binary image is an image on which binarization is performed by using a thresh value with respect to luminance of each pixel of a captured image to more accurately detect a defective image. Reference numerals 402a, 412a, 422a, and 432a denote original images of floating impurities. Reference numerals 402b, 412b, 422b, and 432b denote secondary reflective images of the floating impurities.

FIG. 5 is a table of experiment results regarding fifth through eighth floating impurities relating to the experiment results of FIG. 3. Referring to FIG. 5, reference numerals 501, 511, 521, and 531 denote captured images of a panel having a floating impurity. Reference numerals 502, 512, 522, and 532 denote binary images. Reference numerals 502a, 512a, 522a, and 532a denote original images of floating impurities. Reference numerals 502b, 512b, 522b, and 532b denote secondary reflective images of the floating impurities.

FIG. 6 is a table of experiment results regarding first through fourth actual defects relating to the experiment results of FIG. 3. Referring to FIG. 6, reference numerals 601, 611, 621, and 631 denote captured images of a panel having an actual defect. Reference numerals 602, 612, 622, and 632 denote binary images. Reference numerals 602a, 612a, 622a, and 632a denote original images of actual defects. Reference numerals 602b, 612b, 622b, and 632b denote secondary reflective images of the actual defects.

The experiment results that are the basis of the present embodiment will now be described with reference to FIGS. 3 through 6.

In an image characteristic of a vertical location 301 of a defect, in case of a floating impurity (see FIGS. 4 and 5), the original image 402a, 412a, 422a, 432a, 502a, 512a, or 532a is displayed at a relatively high location on a screen. The secondary reflective image 402b, 412b, 412c, 412d, 422b, 432b, 502b, 502c, 502d, 512b, 522b, or 532b is displayed at a relatively low location on the screen. Thus, according to these image characteristics, an original image and a secondary reflective image of a floating impurity may be distinguished from each other. The image characteristic of a floating impurity related to the vertical location 301 may be changed according to a location of the photographing unit 101 of FIG. 1.

The image characteristic of the vertical location 301 of a defect in a case of an actual defect like a physical or chemical defect such as scratch (see FIG. 6) is the same as in a case of a floating impurity. In other words, the original image 602a, 612a, 622a or 632a is displayed as a relatively high location on a screen. The secondary reflective image 602b, 612b, 622b, or 632b is displayed as a relatively high location on a screen. Thus, according to this image characteristic, an original image and a secondary reflective image of the actual defect may be identified. The image characteristic of a floating impurity related to the vertical location 301 may be changed according to a location of the photographing unit 101 of FIG. 1.

In an image characteristic related to a number 302, in case of a floating impurity (see FIGS. 4 and 5), only one of the original images 402a, 412a, 432a, 502a, 512a, and 532a is displayed on the screen, whereas at least one of the secondary reflective images 402b, 412b, 412c, 412d, 422b, 432b, 502b, 502c, 502d, 512b, 522b, and 532b is displayed on the screen. For example, the three secondary reflective images 412b, 412c, and 412d are displayed on the image 411 of a floating impurity, and the three secondary reflective images 502b, 502c, and 502d are displayed on the image 501 of a floating impurity.

Meanwhile, in case of an actual defect like a physical or chemical defect such as scratch (see FIG. 6), only one of the original image 602a, 612a, 622a, or 632a is displayed on the screen, whereas only one or none of the secondary reflectively images 602b, 612b, 622b or 632b may be displayed on the screen.

Therefore, according to the characteristic of the image number, if secondary reflective images of a defect are plural, the defect may be determined as a floating impurity. Also, if there is no secondary reflective image of a defect, the defect may be determined as an actual defect.

With regard to an image characteristic related to an average luminance 303a of a transparent impurity or a transparent defect, in case of a floating impurity (see FIGS. 4 and 5), the original image 402a, 432a, 502a, or 532a has relatively a low average luminance, whereas the secondary reflective image 402b, 432b, 502b, 502c, 502d, 522b, and 532b has a relatively high average luminance.

In this regard, in case of a transparent actual defect (see FIG. 6), the original image 602a, 612a, 622a, or 632a has an intermediate level of average luminance, and the secondary reflective image 602b, 612b, 622b, or 632b also has an intermediate level of average luminance. That is, in case of the transparent actual defect, a difference in average luminance between the original image and the secondary reflective image is relatively small.

In an image characteristic related to an average luminance 303b of a non-transparent impurity, the original image 412a, 422a, or 512a has a relatively high average luminance, whereas the secondary reflective image 412b, 412c, 412d, 422d, or 512b has a relatively low average luminance.

For reference, there may be no non-transparent actual defect, and thus, it is set as not applicable (N/A).

Therefore, the image characteristics related to the average luminances 303a and 303b are summarized as below.

In case of a floating impurity, a difference in average luminance between an original image and a secondary reflective image is relatively great, whereas, in case of an actual defect, the difference in average luminance between the original image and the secondary reflective image is relatively small.

Therefore, the image characteristics related to the average luminances 303a and 303b are used as described below.

If a difference in average luminance between an original image and a secondary reflective image of a defect is greater than a predetermined value, the defect may be determined as a floating impurity, whereas the difference in average luminance between the original image and the secondary reflective image of the defect is not greater than the predetermined value, the defect may be determined as an actual defect.

FIG. 7 shows a plurality of partial regions A through P partitioned from an overall region 701 of a captured image to perform operation S203 of FIG. 2. FIG. 8 is a detailed flowchart of operation S203 of FIG. 2 in which a variance value of the captured image is calculated. Operation S203 will now be described in detail with reference to FIGS. 1, 7, and 8.

The defect determining unit 102 calculates a sum of luminance values of the plurality of partial regions A through P (S801).

The defect determining unit 102 calculates an average value of the calculated sum of luminance values (S803).

The defect determining unit 102 calculates deviations of the calculated sum of luminance values with respect to the average value (S805), and calculates a variance value of the captured image based on the calculated deviations (S807).

An equation of the above-described method of obtaining the variance value is well known, and thus, a description thereof is omitted here.

FIG. 9 is a detailed flowchart of operation S211 of FIG. 2 in which an original image and a secondary reflective image of a defect is searched for. FIG. 10 shows a binary image obtained by performing operation S901 of FIG. 9. The binary image of FIG. 10 is merely a brief example for convenience of description and quite many pixels are present. Operation S211 will now be described in detail with reference to FIGS. 1, 9, and 10.

The defect determining unit 102 performs binarization on a luminance of each pixel of a captured image by using a threshold value to identify a background region and a non-background region of the captured image (S901). In FIG. 10, reference numeral 1001 denotes a binary image and reference numerals 1001A and 1001B denote non-background regions.

If pixels more than a set number are continuously adjacent to one another in the non-background region 1001A or 1001B, the defect determining unit 102 sets this region as a region of an original image or a secondary reflective image of a defect (S903).

For example, referring to FIG. 10, since pixels more than the set pixel number are continuously adjacent to one another in the non-background region 1001A, the non-background region 1001A is set as the region of the original image or the secondary reflective image of the defect.

Also, since pixels more than the set pixel number are not continuously adjacent to one another in the non-background region 1001B, the non-background region 1001B is not set as the region of the original image or the secondary reflective image of the defect.

After setting the region of the original image or the secondary reflective image of the defect in operation 903, the defect determining unit 102 determines if the number of the set region is only one (S905). If only one region is set in operation S903, the defect determining unit 102 sets this region as the original image of the defect (S907). In this case, since there is no secondary reflective image, the defect is determined as an actual defect. Accordingly, an inspection target panel is determined to fail in operations S213 and S219 of FIG. 2.

If more than one region is set as a region of an original image or a secondary reflective image of a defect in operation 903, the defect determining unit 102 identifies the original image of the defect by a vertical location comparison on a screen (S909). The defect determining unit 102 identifies at least one region, other than a region of the original image, among the more than one region as a secondary reflective image (S911).

Figure 11:
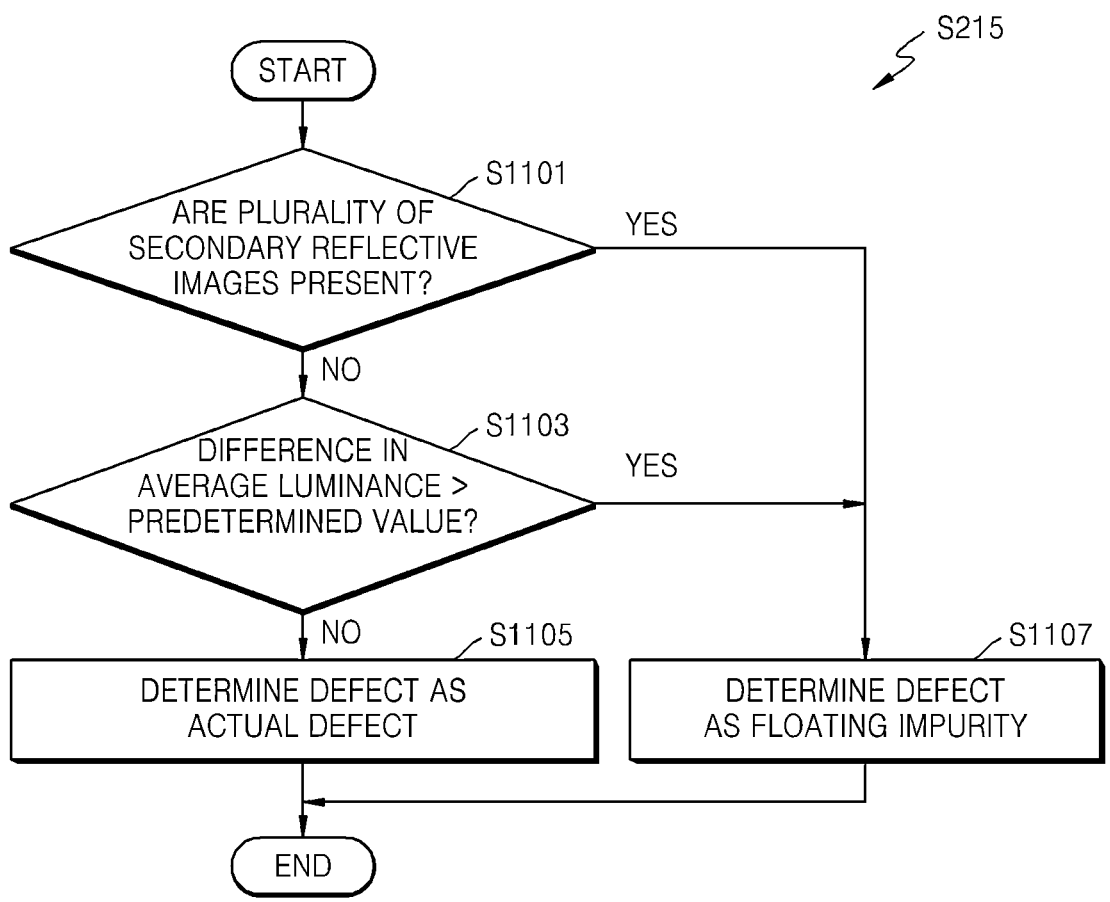
FIG. 11 is an exemplary detailed flowchart of operation S215 of FIG. 2, according to an exemplary embodiment.

FIG. 11 is an exemplary detailed flowchart of operation S215 of FIG. 2 in which whether the defect is a floating impurity or an actual defect is determined. Operation S215 of FIG. 2 will now be described in detail with reference to FIGS. 1 and 11.

The defect determining unit 102 determines whether an image captured by the photographing unit 101 has more than one secondary reflective image (S1101).

If the captured image has more than one secondary reflective image, the defect determining unit 102 determines the defect as a floating impurity (S1101 and S1107). For example, if the defect corresponds to the image 411 of FIG. 4 or the image 501 of FIG. 5, the defect is determined as a floating impurity.

If the captured image does not have more than one secondary reflective image, the defect determining unit 102 determines whether a difference in average luminance between the original image and the secondary reflective image of the defect is greater than a predetermined value (S1103).

If the difference in average luminance between the original image and secondary reflective image of the defect is greater than the predetermined value, the defect determining unit 102 determines the defect as a floating impurity (S1103 and S1107).

If the difference in average luminance between the original image and secondary reflective image of the defect is not greater than the predetermined value, the defect determining unit 102 determines the defect as an actual defect (S1103 and S1105).

Although one predetermined value used in determining between the floating impurity and the actual defect in the example of FIG. 11, more than one predetermined value different from one another may be used for an intermediate range of the different predetermined values for more precise inspection of a panel defect.

Figure 12:
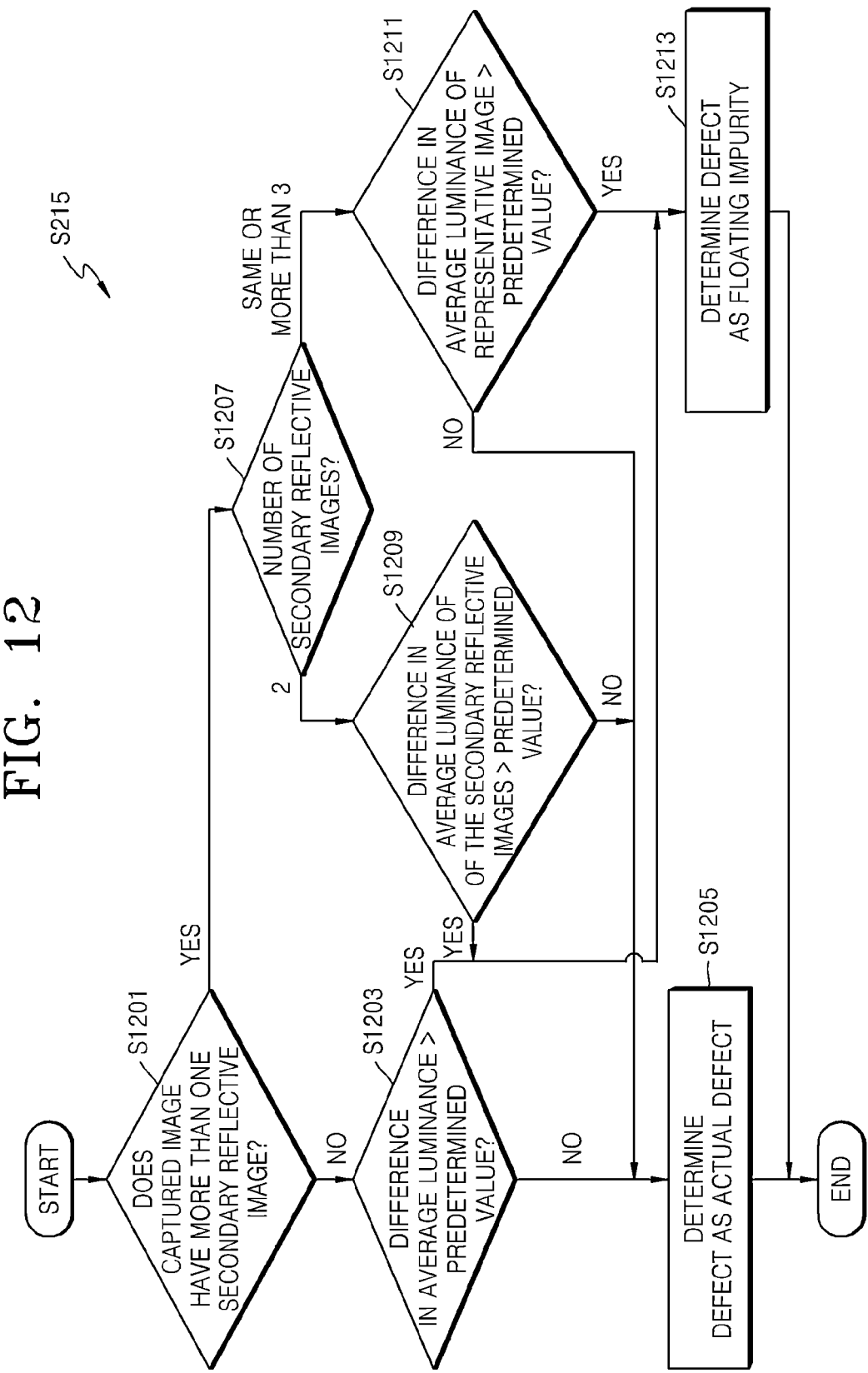
FIG. 12 is another exemplary detailed flowchart of operation S215 of FIG. 2, according to an exemplary embodiment.

FIG. 12 is another exemplary detailed flowchart of operation S215 of FIG. 2 in which whether the defect is a floating impurity or an actual defect is determined. Operation S215 of FIG. 2 will now be described in detail with reference to FIGS. 1 and 12.

The defect determining unit 102 determines whether the captured image has more than one secondary reflective image (S1201).

If the captured image does not have more than one secondary reflective image, the defect determining unit 102 determines whether a difference in average luminance between an original image and a secondary reflective image of a defect is greater than a predetermined value (S1203).

If the difference in average luminance between the original image and the secondary reflective image of the defect is greater than the predetermined value, the defect determining unit 102 determines the defect as a floating impurity (S1203 and S1213).

If the difference in average luminance between the original image and the secondary reflective image of the defect is not greater than the predetermined value, the defect determining unit 102 determines the defect as an actual defect (S1203 and S1205).

Although one predetermined value is used in operations S1203, S1205, and S1213, more than one predetermined value different from one another may be used for an intermediate range of the different predetermined values for more precise inspection of a panel defect.

If the defect determining unit 102 determines that the captured image has more than one secondary reflective image in operation S1201, the defect determining unit 102 determines the number of the secondary reflective images (S1207).

If the number of the secondary reflective images is two in operation S1207, the defect determining unit 102 determines whether a difference in average luminance between the original image and the two secondary reflective images of the defect is greater than the predetermined value (S1209).

If the difference in average luminance between the original image and the two secondary reflective images of the defect is greater than the predetermined value, the defect determining unit 102 determines the defect as a floating impurity (S1209 and S1213).

If the difference in average luminance between the original image and the two secondary reflective images of the defect is not greater than the predetermined value, the defect determining unit 102 determines the defect as an actual defect (S1209 and S1205).

More than two predetermined values may be used to determine whether a defect is a floating impurity or an actual defect.

If the number of the secondary reflective images is more than two like the image 411 of FIG. 4 or the image 501 of FIG. 5 in operation S1207, the defect determining unit 102 determines whether a difference in average luminance between the original image and a representative secondary reflective image of the defect is greater than the predetermined value (S1211).

In the present embodiment, the representative secondary reflective image is the largest image among the secondary reflective images. For example, in secondary reflective images of the image 411 of FIG. 4, the region 412b of may be the representative secondary reflective image. In secondary reflective images of the image 501 of FIG. 4, the region 502b may be the representative secondary reflective image.

If a processing speed of the defect determining unit 102 is relatively fast, an average luminance of the representative secondary reflective image is not used but an average luminance of all the secondary reflective images may be used.

Next, if the difference in average luminance between the original image and the representative secondary reflective image of the defect is greater than the predetermined value, the defect determining unit 102 determines the defect as a floating impurity (S1211 and S1213).

If the difference in average luminance between the original image and the representative secondary reflective image of the defect is not greater than the predetermined value, the defect determining unit 102 determines the defect as an actual defect (S1211 and S1205).

Again, more than one predetermined value may be used in determining whether a defect is a floating impurity and an actual defect in operation 215 of FIG. 2.

As described above, the panel inspection method and the panel inspection apparatus employing the panel inspection method according to the exemplary embodiments may determine whether a defect is an actual defect or a floating impurity by using a characteristic difference between an original image and a secondary reflective image of the defect even if a variance value of luminance of a captured image is greater than a reference value. That is, if the defect is a floating impurity, an inspection target panel may be successfully processed as a good product.

Accordingly, even if the inspection target panel has no actual defect, a failure frequency of the inspection target panel may be minimized, thereby increasing the panel productivity.

While the inventive concept has been particularly shown and described with reference to the above exemplary embodiments thereof, it will be understood by those of ordinary skill in the art that various changes in form and details may be made therein without departing from the spirit and scope of the inventive concept as defined by the following claims.

What is claimed is:

1. A panel inspection method comprising:
   (a) determining whether a variance value of luminance of a captured image of a panel is greater than a reference value, and searching for an original image and at least one secondary reflective image of a defect of the panel if it is determined that the variance value is greater than the reference value; and
   (b) determining whether the defect is an actual defect or an impurity disposed on the panel based on at least one of a difference in a luminance characteristic between the original image and the secondary reflective image and a number of the searched secondary reflective image,
   wherein the captured image comprises the original image from a primary reflection from the panel and the secondary reflective image from a secondary reflection from the panel.

2. The panel inspection method of claim 1, further comprising calculating the variance value of luminance of the captured image in operation (a), wherein the calculating the variance value comprises:
  partitioning a region of the captured image into a plurality of partial regions;
  calculating a sum of luminance values of the plurality of partial regions;
  calculating an average value of the calculated sum of the luminance values;
  calculating deviations of the sum of the luminance values with respect to the average value of the calculated sum of the luminance values; and
  obtaining the variance value of the luminance of the captured image of the panel.

3. The panel inspection method of claim 1, wherein operation (b) comprises determining the defect as the actual defect if it is determined that there is no secondary reflective image as a result of the searching for the original image and the secondary reflective image of the defect.

4. The panel inspection method of claim 1, wherein the searching for the original image and the secondary reflective image of the defect in operation (a) comprises:
  performing binarization on a luminance of each pixel of the captured image by using a threshold value to identify a background region and a non-background region of the captured image;
  determining if pixels more than a set number are continuously adjacent to one another in the non-background region; and
  setting the non-background region as a region of the original image or the secondary reflective image of the defect if it is determined that pixels more than the set number are continuously adjacent to one another in the non-background region.

5. The panel inspection method of claim 4, wherein operation (a) further comprises:
  determining if more than one region is set as the region of the original image or the secondary reflective image of the defect; and
  if it is determined that more than one region is set, identifying regions of the original image and the secondary reflective image by a vertical location comparison on a screen of the captured image.

6. The panel inspection method of claim 1, wherein operation (b) further comprises determining the defect as the impurity, if it is determined that there is more than one secondary reflective image as a result of the searching for the original image and the secondary reflective image of the defect.

7. The panel inspection method of claim 1, wherein operation (b) further comprises determining the defect as the impurity if it is determined that a difference in average luminance between the original image and the secondary reflective image is greater than a predetermined value.

8. The panel inspection method of claim 1, wherein operation (b) further comprises:
  determining if the number of the searched secondary reflective image more than one;
  determining if a difference in average luminance between the original image and a representative secondary reflective image among the more than one secondary reflective image is greater than a predetermined value; and
  determining the defect as the impurity if it is determined that the difference in average luminance between the original image and the representative secondary reflective image is greater than the predetermined value.

9. The panel inspection method of claim 7, wherein, in operation (b), the representative secondary reflective image is the largest image among the more than one secondary reflective image.

10. The panel inspection method of claim 1, wherein operation (b) further comprises:
  determining if the number of the searched secondary reflective image is more than one;
  determining if a difference in average luminance between the original image and the more than one secondary reflective image is greater than a predetermined value; and
  determining the occurred defect as the impurity if it is determined that the difference in average luminance between the original image and the more than one secondary reflective image is greater than the predetermined value.

11. A panel inspection apparatus comprising:
  a defect determining unit configured to analyze a captured image of a panel and determine whether a defect is present in the panel, wherein the defect determining unit is further configured to determine whether a variance value of luminance of the captured image is greater than a reference value, and search for an original image and at least one secondary reflective image of the defect of the panel if it is determined that the variance value is greater than the reference value; and determine whether the defect is an actual defect or a impurity based on at least one of a difference in a luminance characteristic between the original image and the secondary reflective image and a number of the searched secondary reflective image,
  wherein the captured image comprises the original image from a primary reflection from the panel and the secondary reflective image from a secondary reflection from the panel.

12. The panel inspection apparatus of claim 11, wherein the defect determining unit is further configured to calculate the variance value of luminance of the captured image by partitioning a region of the captured image into a plurality of partial regions, calculating a sum of luminance values of the plurality of partial regions, calculating an average value of the calculated sum of the luminance values, calculating deviations of the sum of the luminance values with respect to the average value of the calculated sum of the luminance values, and obtaining the variance value of the luminance of the captured image of the panel.

13. The panel inspection apparatus of claim 11, wherein the defect determining unit is configured to determine the defect as the actual defect if the determining unit determines that there is no secondary reflective image as a result of the searching for the original image and the secondary reflective image of the defect.

14. The panel inspection apparatus of claim 11, wherein, to search for the original image and the secondary reflective image of the defect, the defect determining unit is configured to perform binarization on a luminance of each pixel of the captured image by using a threshold value to identify a background region and a non-background region of the captured image, determine if pixels more than a set number are continuously adjacent to one another in the non-background region, and set the non-background region as a region of the original image or the secondary reflective image of the defect if it is determined that pixels more than the set number are continuously adjacent to one another in the non-background region.

15. The panel inspection apparatus of claim 14, wherein, to search for the original image and the secondary reflective image of the defect, the defect determining unit is configured to determine if more than one region is set as the region of the original image or the secondary reflective image of the defect, and identify regions of the original image and the secondary reflective image by a vertical location comparison on a screen of the captured image, if it is determined that more than one region is set as the region of the original image or the secondary reflective image of the defect.

16. The panel inspection apparatus of claim 11, wherein the defect determining unit is configured to determine the defect as the impurity if it is determined that there is more than one secondary reflective image as a result of the searching for the original image and the secondary reflective image of the defect.

17. The panel inspection apparatus of claim 11, wherein the defect determining unit is configured to determine the defect as the impurity if it is determined that a difference in average luminance between the original image and the secondary reflective image is greater than a predetermined value.

18. The panel inspection apparatus of claim 17, wherein the defect determining unit is configured to determine if the number of the searched secondary reflective image is more than one, determine if a difference in average luminance between the original image and a representative secondary reflective image among the more than one secondary reflective image is greater than a predetermined value, and determine the defect as the impurity if it is determined that the difference in average luminance between the original image and the representative secondary reflective image is greater than the predetermined value.

19. The panel inspection apparatus of claim 11, wherein the defect determining unit is configured to determine if the number of the searched secondary reflective images is more than one, determine if a difference in average luminance between the original image and the more than one secondary reflective image is greater than a predetermined value, and determine the defect as the impurity if it is determined that the difference in average luminance between the original image and the more than one secondary reflective image is greater than the predetermined value.

20. The panel inspection apparatus of claim 18, wherein the representative secondary reflective image is the largest image among the more than one secondary reflective image.

* * * * *